United States Patent
Tanabe et al.

(10) Patent No.: US 12,161,436 B2
(45) Date of Patent: Dec. 10, 2024

(54) ROBOTIC SURGICAL SYSTEM, CONTROL DEVICE OF ROBOTIC SURGICAL SYSTEM, AND CONTROL METHOD OF ROBOTIC SURGICAL SYSTEM

(71) Applicants: KAWASAKI JUKOGYO KABUSHIKI KAISHA, Kobe (JP); MEDICAROID CORPORATION, Kobe (JP)

(72) Inventors: Masataka Tanabe, Akashi (JP); Tomohiro Hayashida, Kobe (JP); Yuto Shintani, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 581 days.

(21) Appl. No.: 17/503,615

(22) Filed: Oct. 18, 2021

(65) Prior Publication Data

US 2022/0125536 A1  Apr. 28, 2022

(30) Foreign Application Priority Data

Oct. 23, 2020  (JP) .................................. 2020-177743

(51) Int. Cl.
*A61B 34/37* (2016.01)
*A61B 34/00* (2016.01)
*A61B 34/20* (2016.01)
*A61B 34/30* (2016.01)
*G05B 19/19* (2006.01)

(52) U.S. Cl.
CPC .............. *A61B 34/37* (2016.02); *A61B 34/20* (2016.02); *A61B 34/30* (2016.02); *A61B 34/75* (2016.02); *A61B 34/77* (2016.02); *G05B 19/19* (2013.01); *G05B 2219/34042* (2013.01); *G05B 2219/45117* (2013.01)

(58) Field of Classification Search
CPC ......... A61B 34/37; A61B 34/20; A61B 34/30; A61B 34/75; A61B 34/77; A61B 34/70; G05B 19/19; G05B 2219/34042; G05B 2219/45117
See application file for complete search history.

(56) References Cited

U.S. PATENT DOCUMENTS

| | | | | |
|---|---|---|---|---|
| 4,986,150 A | * | 1/1991 | Okazaki | B23Q 1/36 82/158 |
| 7,865,269 B2 | | 1/2011 | Prisco et al. | |
| 2004/0243147 A1 | * | 12/2004 | Lipow | A61B 34/74 606/130 |

(Continued)

FOREIGN PATENT DOCUMENTS

| | | | | |
|---|---|---|---|---|
| CN | 110320858 B | * | 5/2022 | ............. F02B 77/13 |
| JP | 2008-004007 A | | 1/2008 | |

OTHER PUBLICATIONS

CN-110320858-B translation (Year: 2022).*
Reversible_Position_Domain_Notch_Filter_for_Suppressing_Vibrations_Caused_by_Kinematic_Errors_in_Flexible_Joint_Robots (Year: 2024).*

*Primary Examiner* — Kyle T Johnson
(74) *Attorney, Agent, or Firm* — METROLEX IP LAW GROUP, PLLC; Robert L. Scott, Esq.

(57) ABSTRACT

A robotic surgical system includes a controller configured or programmed to calculate an operation speed signal, to calculate a first filtered signal, to calculate a limited signal, to calculate a second filtered signal, and calculate an output position signal based on the second filtered signal.

20 Claims, 13 Drawing Sheets

(56) References Cited

U.S. PATENT DOCUMENTS

| | | | |
|---|---|---|---|
| 2007/0142968 A1* | 6/2007 | Prisco | A61B 1/00193 700/264 |
| 2008/0010706 A1* | 1/2008 | Moses | A61B 34/30 600/407 |
| 2009/0248038 A1* | 10/2009 | Blumenkranz | A61B 34/30 606/130 |
| 2010/0094312 A1* | 4/2010 | Ruiz Morales | A61B 34/70 73/504.03 |
| 2016/0030119 A1* | 2/2016 | Devengenzo | A61B 34/37 606/130 |
| 2018/0028269 A1* | 2/2018 | Morel | A61B 34/76 |
| 2018/0168749 A1* | 6/2018 | Dozeman | A61B 34/30 |
| 2020/0073343 A1* | 3/2020 | Tsuneki | G05B 19/19 |
| 2022/0125536 A1* | 4/2022 | Tanabe | A61B 34/77 |
| 2023/0263587 A1* | 8/2023 | Pandya | A61B 34/77 606/1 |

\* cited by examiner

TCP2
TCP

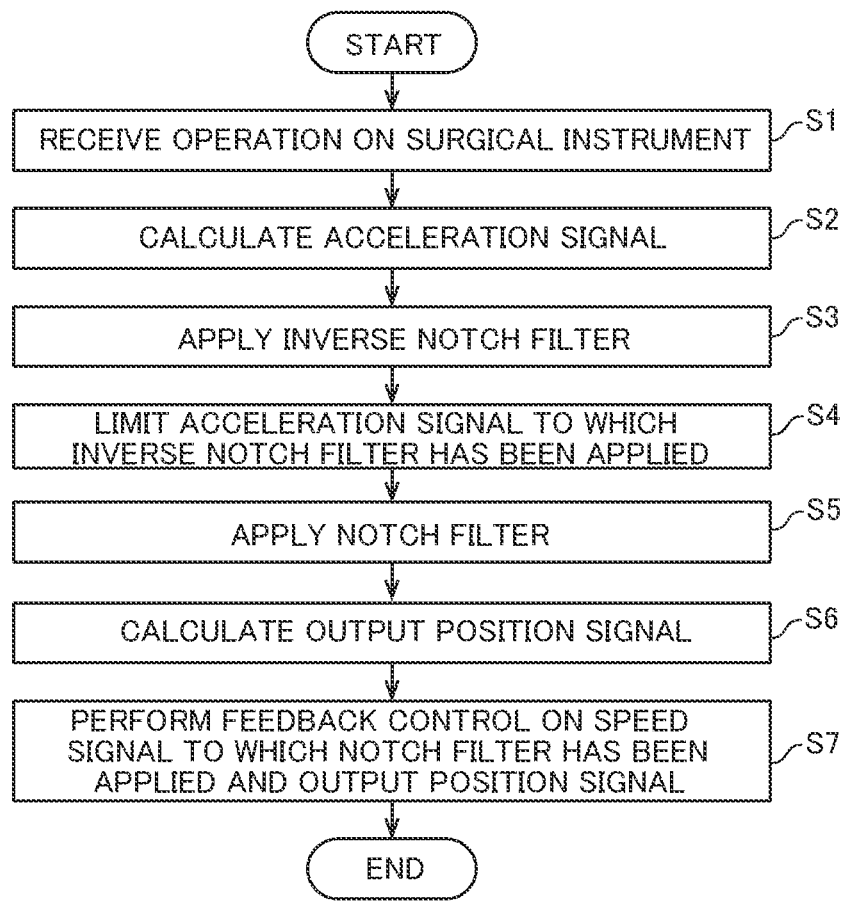

ROBOTIC SURGICAL SYSTEM, CONTROL DEVICE OF ROBOTIC SURGICAL SYSTEM, AND CONTROL METHOD OF ROBOTIC SURGICAL SYSTEM

CROSS-REFERENCE TO RELATED APPLICATION

The present application claims priority to JP2020-177743, which is incorporated herein by reference.

BACKGROUND OF THE INVENTION

Field of the Invention

The present disclosure relates to a robotic surgical system, a control device of a robotic surgical system, and a control method of a robotic surgical system, and more particularly, it relates to a robotic surgical system, a control device of a robotic surgical system, and a control method of a robotic surgical system to control the operation of a surgical instrument based on an operation received by an operation unit.

Description of the Background Art

Conventionally, a robotic surgical system to control movement of a surgical instrument based on an operation received by an operation unit is known.

U.S. Pat. No. 7,865,269 discloses a robotic surgical system including a console including a master manipulator (operation unit) operated by a surgeon, and a slave manipulator (manipulator arm) that moves based on a surgeon's operation received by the master manipulator. In this robotic surgical system, a tool (surgical instrument) is provided at the end of the slave manipulator. The slave manipulator includes a plurality of links connected by joints.

In the robotic surgical system disclosed in U.S. Pat. No. 7,865,269, joint controllers are provided so as to correspond to the joints of the slave manipulator (manipulator arm). The joint controllers apply a linear filter to joint position command values from the master manipulator side. Then, the joint position command values to which the linear filter has been applied are transmitted to the joints to drive the joints. Thus, vibrations of the joint position command values (signals) are reduced by the linear filter, and thus when the slave manipulator is operated based on the joint position command values, vibrations of the slave manipulator can be reduced. Furthermore, the joint controllers feed back joint position information detected by an encoder to the master manipulator side. The linear filter described above causes a control delay, and thus in U.S. Pat. No. 7,865,269, an inverse filter is provided in the feedback path to compensate for the control delay.

However, in the robotic surgical system disclosed in U.S. Pat. No. 7,865,269, the inverse filter for compensating for the control delay is provided in the path for feeding back the joint position information of the slave manipulator detected by the encoder to the master manipulator side. Therefore, in the robotic surgical system disclosed in U.S. Pat. No. 7,865,269, the vibrations of the joint position command values (signals) transmitted from the master manipulator (operator-side apparatus) side to the slave manipulator (patient-side apparatus) side can be reduced by the linear filter, but it is not possible to compensate for (reduce) the control delay in the joint position command values (signals) transmitted from the master manipulator (operator-side apparatus) side to the slave manipulator (patient-side apparatus) side.

SUMMARY OF THE INVENTION

The present disclosure is intended to solve the above problem. The present disclosure aims to provide a robotic surgical system, a control device of a robotic surgical system, and a control method of a robotic surgical system each capable of reducing a control delay while reducing vibrations in a signal transmitted from the operator-side apparatus side to the patient-side apparatus side to reduce vibrations of a patient-side apparatus.

In order to attain the aforementioned object, a robotic surgical system according to a first aspect of the present disclosure includes a patient-side apparatus including a manipulator arm to which a surgical instrument is attached to a tip end side of the manipulator arm, an operator-side apparatus including an operation unit to receive an operation on the surgical instrument, and a controller configured or programmed to output an output position signal indicating a position of the surgical instrument based on an input position signal indicating the position of the surgical instrument corresponding to the received operation, the controller being configured or programmed to control operation of the surgical instrument. The controller is configured or programmed to calculate an operation speed signal that is a signal relating to an operation speed of the surgical instrument based on the input position signal, apply a first filter that amplifies a component of a first frequency band of the calculated operation speed signal to the operation speed signal to calculate a first filtered signal, limit the first filtered signal to calculate a limited signal, apply a second filter that reduces the component of the first frequency band to the limited signal to calculate a second filtered signal, and calculate the output position signal based on the second filtered signal. The operation speed signal is a concept including any one of a speed signal, an acceleration signal, and a jerk signal.

A control device of a robotic surgical system according to a second aspect of the present disclosure is a control device of a robotic surgical system including a patient-side apparatus including a manipulator arm to which a surgical instrument is attached to a tip end side of the manipulator arm, and an operator-side apparatus including an operation unit to receive an operation on the surgical instrument, and includes a controller configured or programmed to output an output position signal indicating a position of the surgical instrument based on an input position signal indicating the position of the surgical instrument corresponding to the received operation, the controller being configured or programmed to control operation of the surgical instrument. The controller is configured or programmed to calculate an operation speed signal that is a signal relating to an operation speed of the surgical instrument based on the input position signal, apply a first filter that amplifies a component of a first frequency band of the calculated operation speed signal to the operation speed signal to calculate a first filtered signal, limit the first filtered signal to calculate a limited signal, apply a second filter that reduces the component of the first frequency band to the limited signal to calculate a second filtered signal, and calculate the output position signal based on the second filtered signal.

A control method of a robotic surgical system according to a third aspect of the present disclosure is a control method of a robotic surgical system including a patient-side apparatus including a manipulator arm to which a surgical instrument is attached to a tip end side of the manipulator arm, an operator-side apparatus including an operation unit to receive an operation on the surgical instrument, and a controller, and includes receiving an operation on the surgical instrument, calculating an operation speed signal that is a signal relating to an operation speed of the surgical instrument based on an input position signal indicating a position of the surgical instrument corresponding to the received operation, applying a first filter that amplifies a component of a first frequency band of the calculated operation speed signal to the operation speed signal to calculate a first filtered signal, limiting the first filtered signal to calculate a limited signal, applying a second filter that reduces the component of the first frequency band to the limited signal to calculate a second filtered signal, and calculating an output position signal indicating the position of the surgical instrument based on the second filtered signal.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 19 is a flowchart for illustrating a control method of the surgical system according to the embodiment of the present disclosure.

DESCRIPTION OF THE PREFERRED EMBODIMENTS

Figure 1:
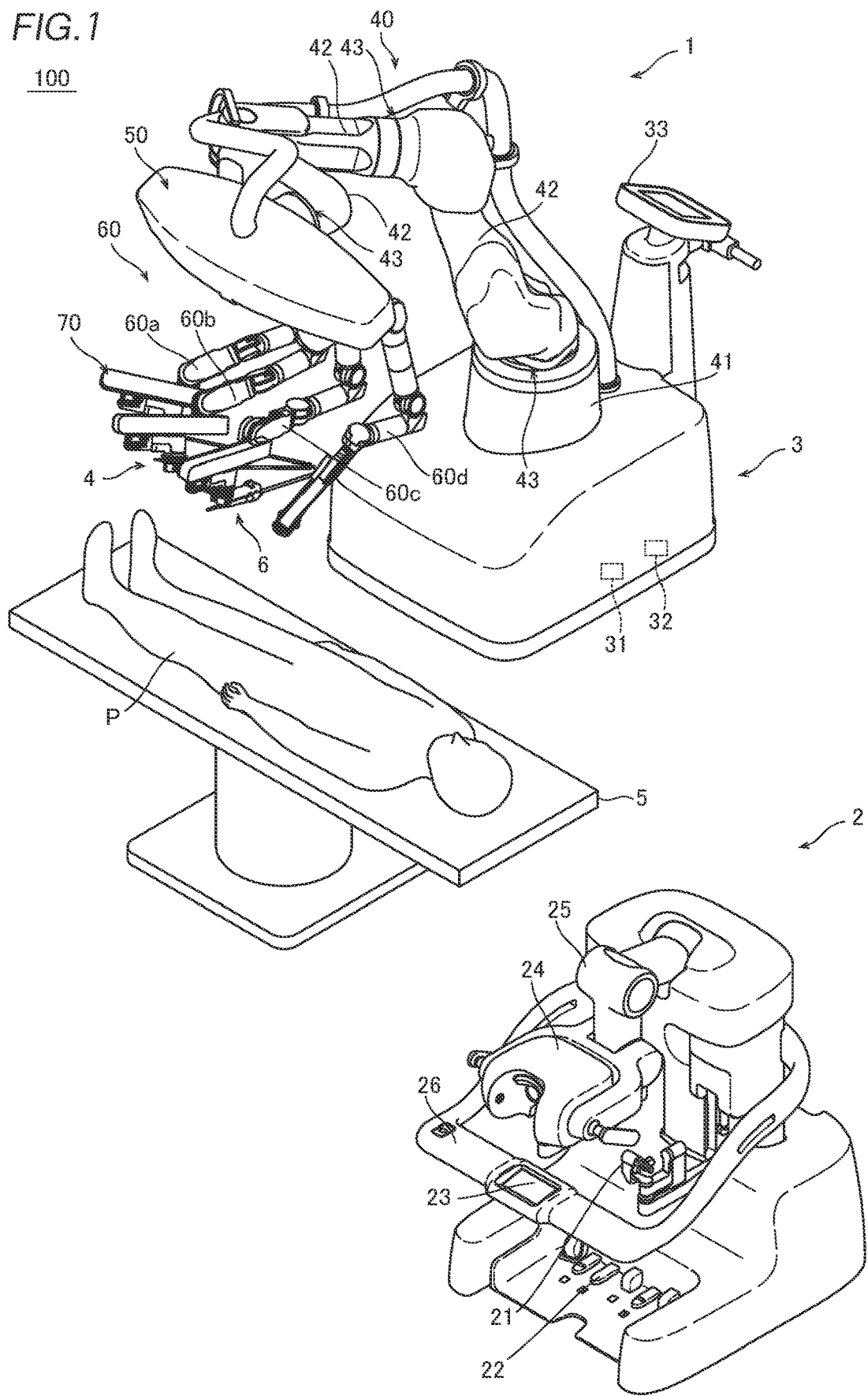
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 18. The surgical system 100 includes a medical manipulator 1 that is a patient P-side device and a remote operation device 2 that is an operator-side apparatus to operate the medical manipulator 1. The medical manipulator 1 includes a medical cart 3 and is movable. The remote operation device 2 is spaced apart from the medical manipulator 1, and the medical manipulator 1 is remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The surgical system 100 is an example of a "robotic surgical system" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The operation manipulator arms 21 define operation handles for the surgeon to input commands. The operation manipulator arms 21 receive the amount of operation for a surgical instrument 4. The monitor 24 is a scope-type display that displays an image captured by an endoscope 6. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1. The operation manipulator arms 21 are examples of an "operation unit" in the claims.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 receives operations to move a positioner 40, an arm base 50, and a plurality of manipulator arms 60 or change their postures mainly in order to prepare for surgery before the surgery.

Figure 2:
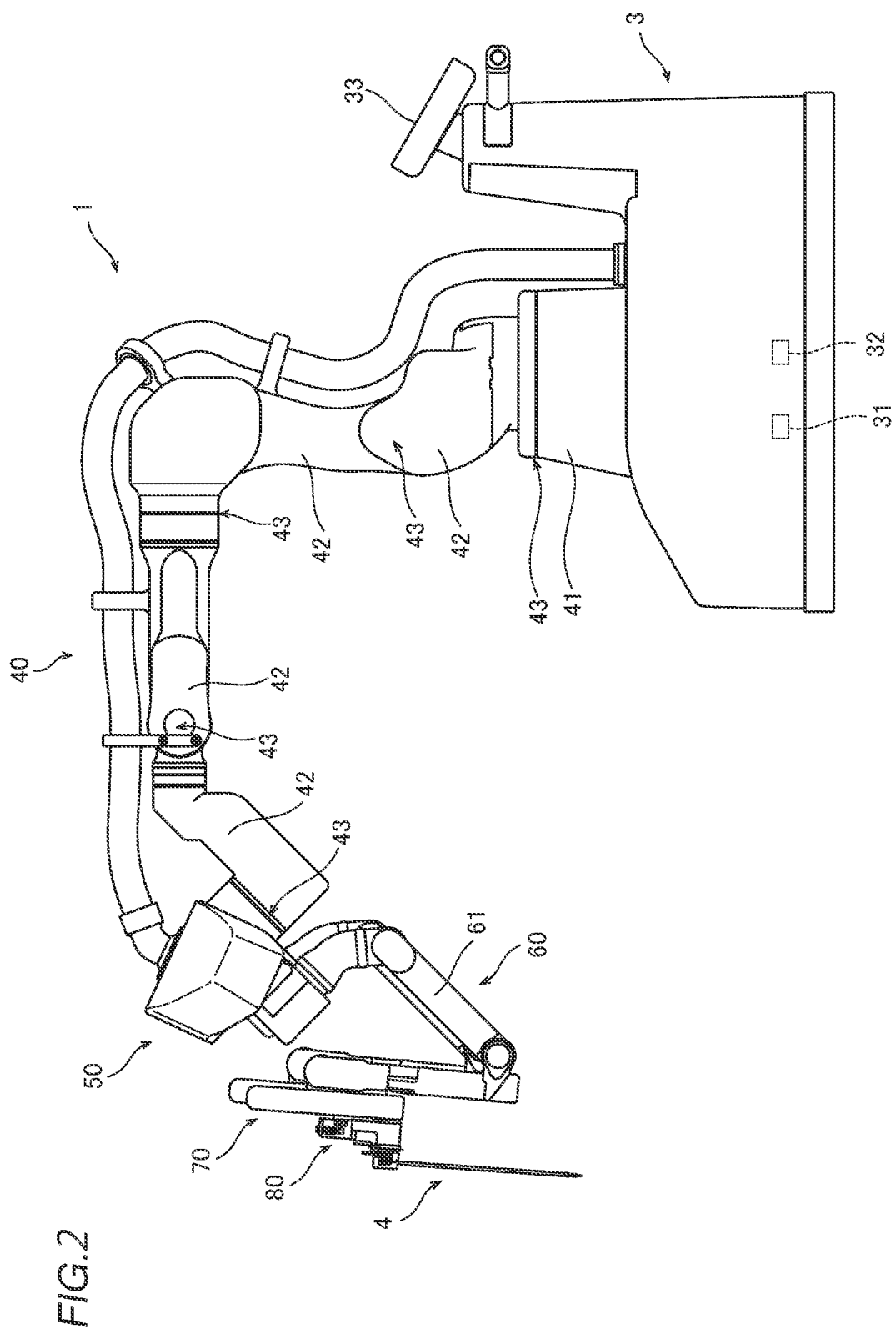
FIG. 2 is a diagram showing the configuration of a medical manipulator according to the embodiment of the present disclosure.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape (long shape). The bases of the plurality of manipulator arms 60 are attached to the arm base 50. Each of the plurality of manipulator arms 60 is able to take a folded posture (stored posture). The arm base 50 and the plurality of manipulator arms 60 are covered with sterile drapes (not shown) and used.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, the surgical instrument 4 is attached to the tip end of each of the plurality of manipulator arms 60. The surgical instrument 4 includes a replaceable instrument or the endoscope 6 (see FIG. 6), for example.

Figure 3:
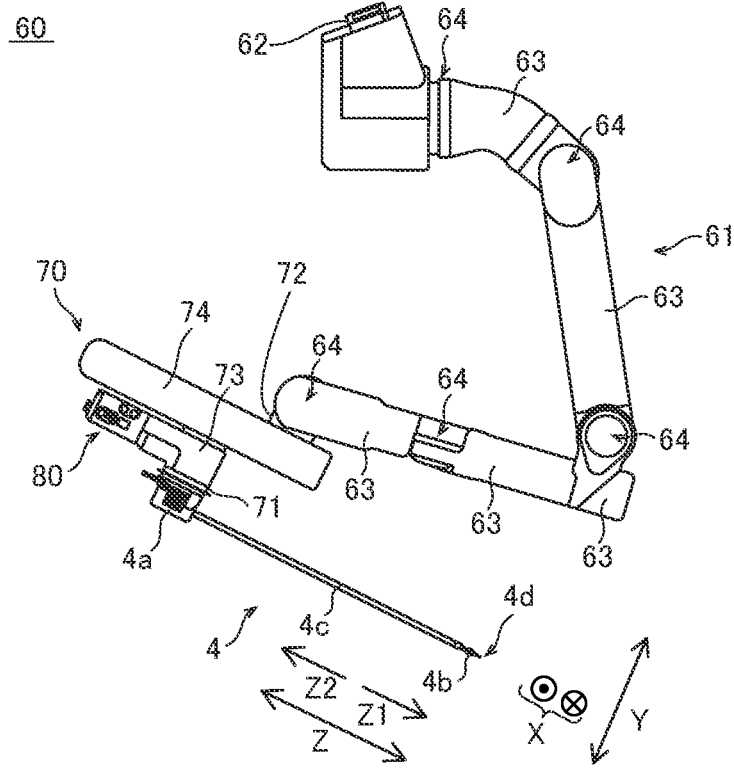
FIG. 3 is a diagram showing the configuration of a manipulator arm according to the embodiment of the present disclosure.

As shown in FIG. 3, the instrument includes a driven unit 4a driven by a servomotor M2 provided in a holder 71 of each of the manipulator arms 60. A pair of forceps 4b is provided at the tip end of the instrument.

Figure 4:
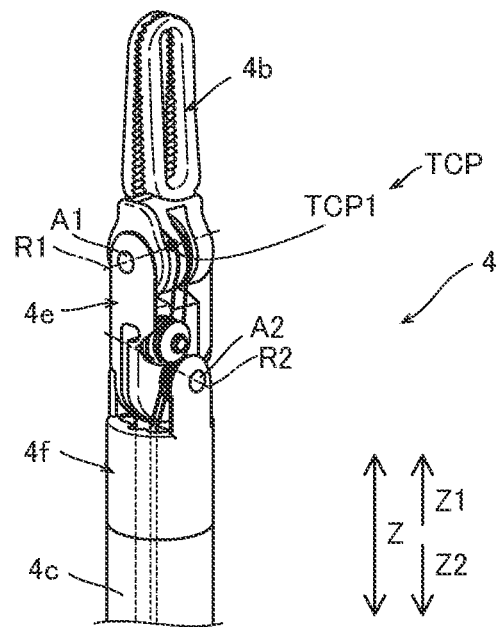
FIG. 4 is a diagram showing a pair of forceps.

As shown in FIG. 4, the instrument includes a first support 4e that supports the pair of forceps 4b such that the pair of forceps 4b is rotatable about a first axis A1, a second support 4f that supports the first support 4e such that the first support 4e is rotatable about a second axis A2, and a shaft 4c connected to the second support 4f. The driven unit 4a, the shaft 4c, the second support 4f, the first support 4e, and the pair of forceps 4b are arranged along a Z direction.

The pair of forceps 4b is attached to the first support 4e so as to rotate about the rotation axis R1 of the first axis A1. The second support 4f supports the first support 4e such that the first support 4e is rotatable about the second axis A2. That is, the first support 4e is attached to the second support 4f so as to rotate about the rotation axis R2 of the second axis A2. A portion of the first support 4e on the tip end side (Zi direction side) has a U-shape. A tool center point (TCP1) is set at the center of the U-shaped portion of the first support 4e on the tip end side in a rotation axis R1 direction.

Figure 6:
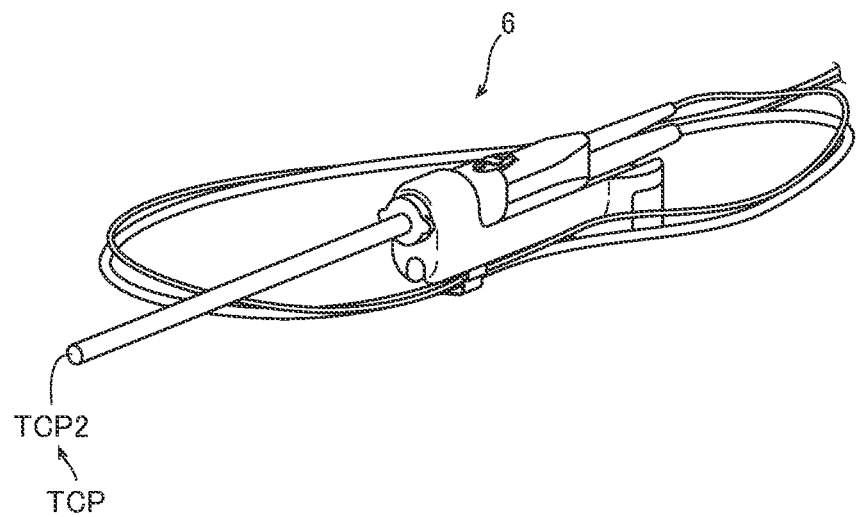
FIG. 6 is a diagram showing an endoscope.
Figure 7:
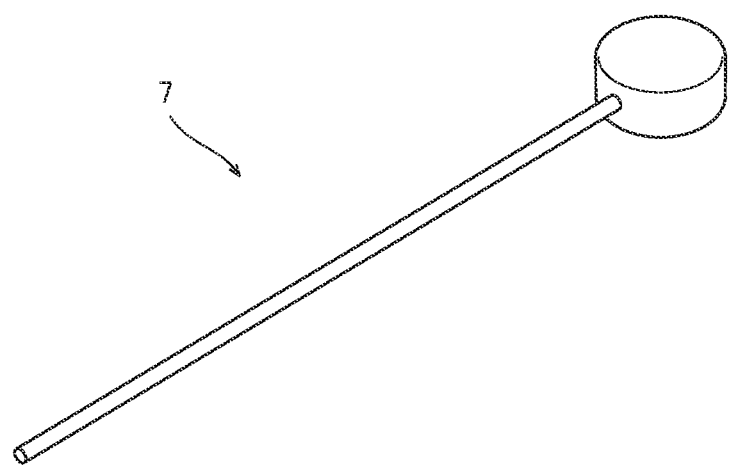
FIG. 7 is a diagram showing a pivot position teaching instrument.

As shown in FIG. 6, a TCP2 of the endoscope 6 is set at the tip end of the endoscope 6.

The configuration of the manipulator arms 60 is now described in detail.

As shown in FIG. 3, each of the manipulator arms 60 includes an arm portion 61 (a base 62, links 63, and joints 64) and a translation mechanism 70 provided at the tip end of the arm portion 61. The tip end sides of the manipulator arms 60 three-dimensionally move with respect to the base sides (arm base 50) of the manipulator arms 60. The plurality of manipulator arms 60 have the same configuration as each other.

The translation mechanism 70 is provided on the tip end side of the arm portion 61, and the surgical instrument 4 is attached thereto. The translation mechanism 70 translates the surgical instrument 4 in a direction in which the surgical instrument 4 is inserted into a patient P. Furthermore, the translation mechanism 70 translates the surgical instrument 4 relative to the arm portion 61. Specifically, the translation mechanism 70 includes the holder 71 that holds the surgical instrument 4. The servomotor M2 (see FIG. 10) is housed in the holder 71. The servomotor M2 rotates a rotating body provided in the driven unit 4a of the surgical instrument 4. The rotating body of the driven unit 4a is rotated such that the pair of forceps 4b is operated.

The arm portion 61 includes a 7-axis articulated robot arm. The arm portion 61 includes the base 62 to attach the arm portion 61 to the arm base 50, and a plurality of links 63 coupled to the base 62. The plurality of links 63 are coupled to each other by the joints 64.

The translation mechanism 70 translates the surgical instrument 4 attached to the holder 71 along the Z direction (a direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the surgical instrument 4 provided on the holder 71 is translated along the Z direction. The tip end of the arm portion 61 is connected to the base end side link 72 so as to rotate the base end side link 72 about an X direction orthogonal to the Z direction.

Figure 5:
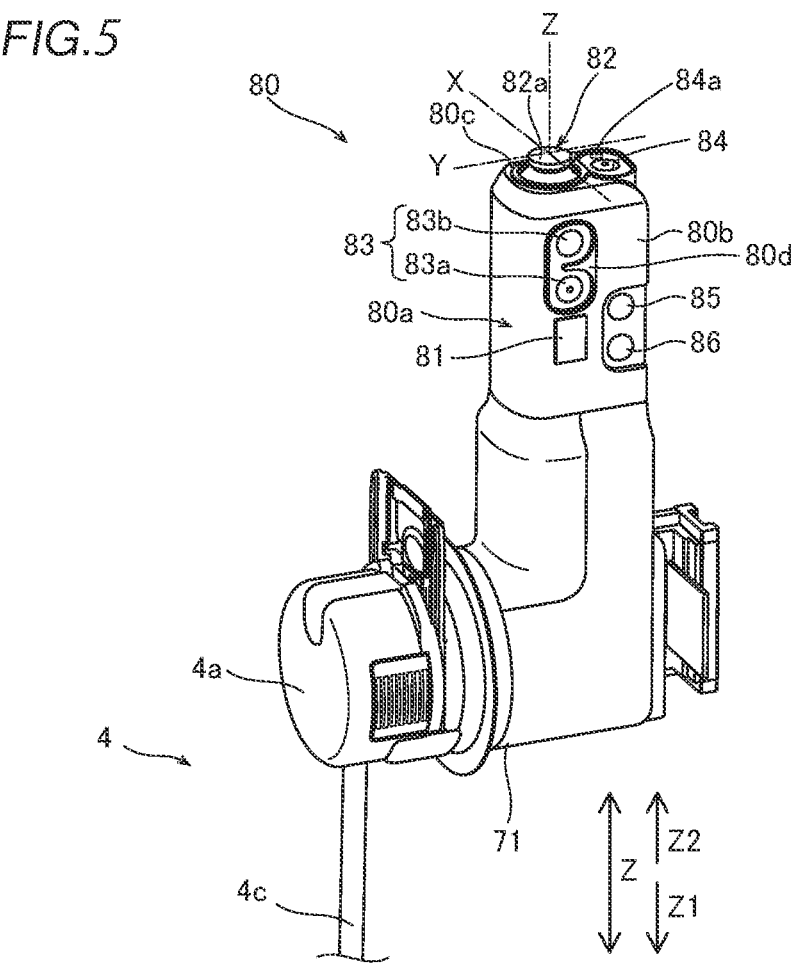
FIG. 5 is a perspective view showing the configuration of an operation unit of the medical manipulator according to the embodiment of the present disclosure.

As shown in FIG. 5, the medical manipulator 1 includes an operation unit 80 attached to each of the manipulator arms 60 to operate the manipulator arm 60. The operation unit 80 includes an enable switch 81, a joystick 82, and a switch unit 83. The enable switch 81 allows or disallows movement of the manipulator arm 60 through the joystick 82 and the switch unit 83. The enable switch 81 gets into a state of allowing movement of the surgical instrument 4 by the manipulator arm 60 when an operator (such as a nurse or an assistant) grasps the operation unit 80 and presses the enable switch 81.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

As shown in FIG. 5, the operation unit 80 includes a pivot button 85 to teach a pivot position PP that serves as a fulcrum (see FIG. 9) for movement of the surgical instrument 4 attached to the manipulator arm 60. The pivot button 85 is provided adjacent to the enable switch 81 on a surface 80b of the operation unit 80. The pivot button 85 is pressed while the tip end of the endoscope 6 (see FIG. 6) or a pivot position teaching instrument 7 (see FIG. 7) is moved to a position corresponding to the insertion position of a trocar inserted into the body surface of the patient P such that the pivot position PP is taught and stored in the storage 32. In the teaching of the pivot position PP, the pivot position PP is set as one point (coordinates), and the direction of the surgical instrument 4 is not set.

As shown in FIG. 1, the endoscope 6 is attached to one manipulator arm 60 (manipulator arm 60c, for example) of the plurality of manipulator arms 60, and surgical instruments 4 other than the endoscope 6 are attached to the remaining manipulator arms 60 (manipulator arms 60a, 60b, and 60d, for example). Specifically, in surgery, the endoscope 6 is attached to one of four manipulator arms 60, and the surgical instruments 4 (such as pairs of forceps 4b) other than the endoscope 6 are attached to the three manipulator arms 60. The pivot position PP is taught with the endoscope 6 attached to the manipulator arm 60 to which the endoscope 6 is to be attached. Furthermore, pivot positions PP are taught with pivot position teaching instruments 7 attached to the manipulator arms 60 to which the surgical instruments 4 other than the endoscope 6 are to be attached. The endoscope 6 is attached to one of two manipulator arms 60 (manipulator arms 60b and 60c) arranged in the center among the four manipulator arms 60 arranged adjacent to each other. That is, the pivot position PP is individually set for each of the plurality of manipulator arms 60.

As shown in FIG. 5, an adjustment button 86 for optimizing the position of the manipulator arm 60 is provided on the surface 80b of the operation unit 80. After the pivot position PP for the manipulator arm 60 to which the endoscope 6 has been attached is taught, the adjustment button 86 is pressed such that the positions of the other manipulator arms 60 (arm base 50) are optimized.

Figure 8:
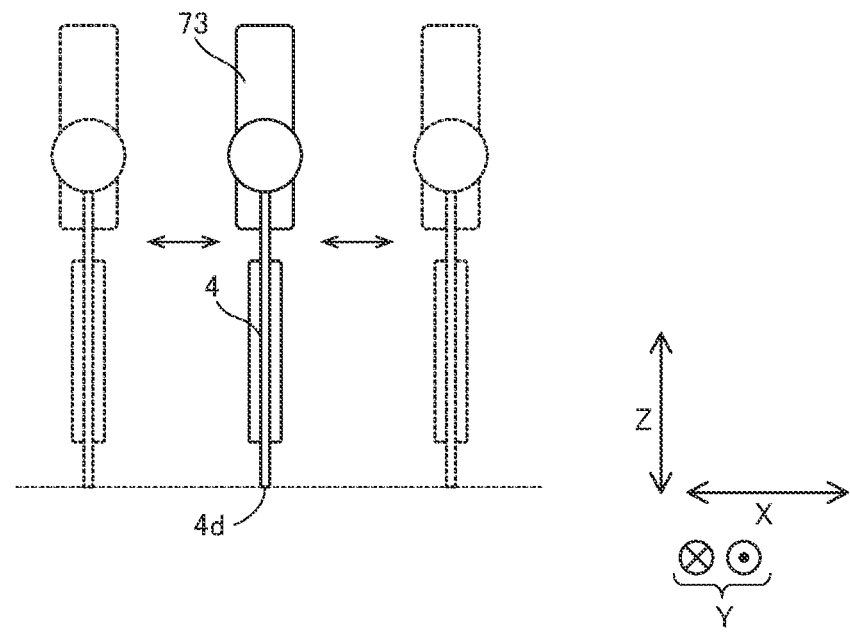
FIG. 8 is a diagram for illustrating translation of the manipulator arm.
Figure 9:
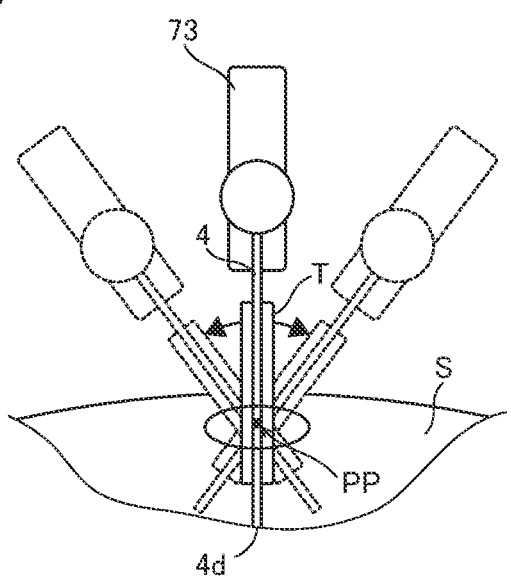
FIG. 9 is a diagram for illustrating rotation of the manipulator arm.

As shown in FIG. 5, the operation unit 80 includes a mode switching button 84 to switch between a mode for translating the surgical instrument 4 attached to the manipulator arm 60 (see FIG. 8) and a mode for rotating the surgical instrument 4 (see FIG. 9). Furthermore, a mode indicator 84a is provided in the vicinity of the mode switching button 84. The mode indicator 84a indicates a switched mode. Specifically, the mode indicator 84a is turned on (rotation mode) or off (translation mode) such that a current mode (translation mode or rotation mode) is indicated.

The mode indicator 84a also serves as a pivot position indicator that indicates that the pivot position PP has been taught.

As shown in FIG. 8, in the mode for translating the manipulator arm 60, the manipulator arm 60 is moved such that the tip end 4d of the surgical instrument 4 moves on an X-Y plane. As shown in FIG. 9, in the mode for rotating the manipulator arm 60, when the pivot position PP is not taught, the manipulator arm 60 is moved such that the surgical instrument 4 rotates about the pair of forceps 4b, and when the pivot position PP is taught, the manipulator arm 60 is moved such that the surgical instrument 4 rotates about the pivot position PP as a fulcrum. The surgical instrument 4 is rotated while the shaft 4c of the surgical instrument 4 is inserted into the trocar.

Figure 10:
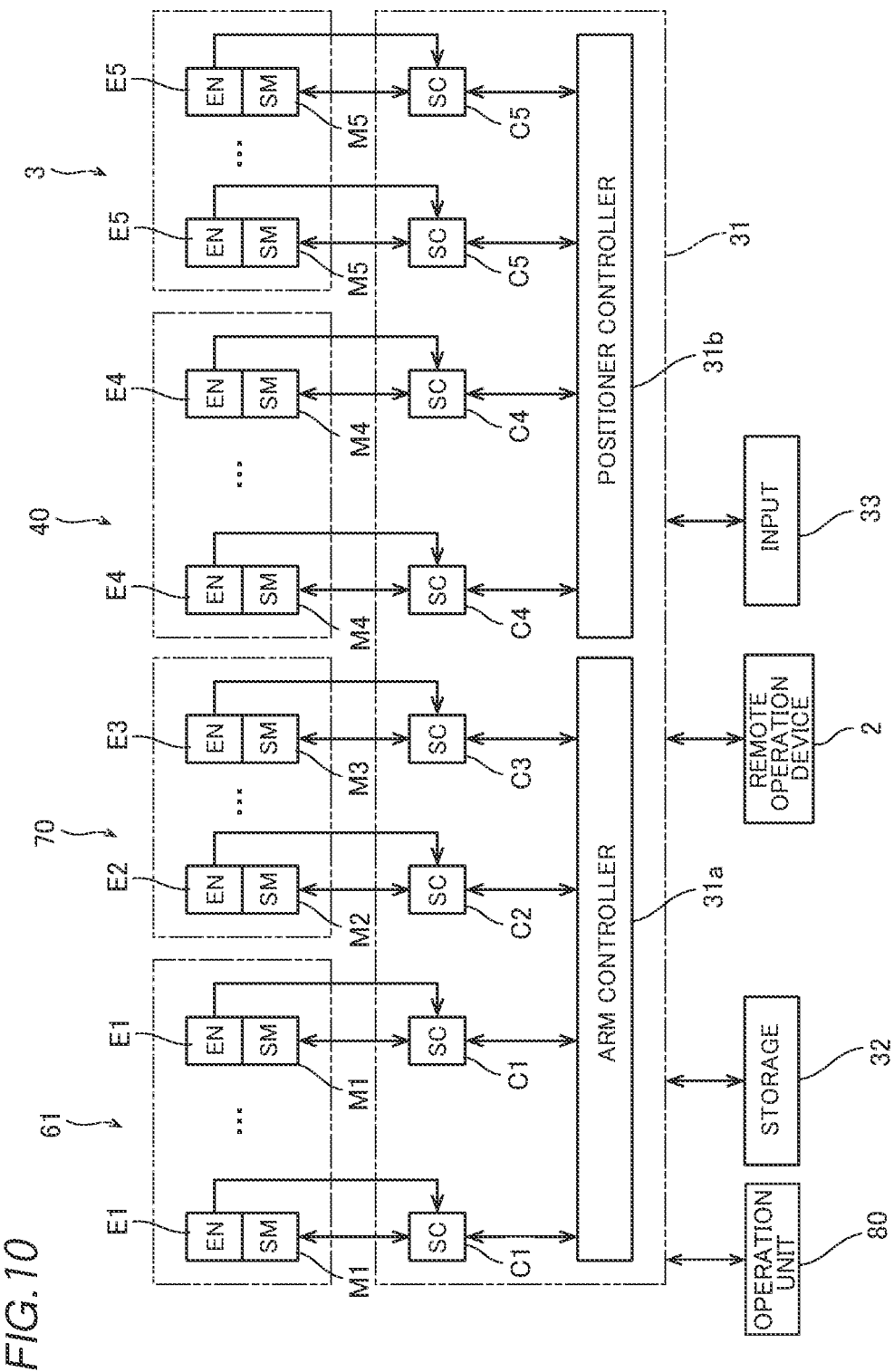
FIG. 10 is a block diagram showing the configuration of a controller of the medical manipulator according to the embodiment of the present disclosure.

As shown in FIG. 10, the manipulator arm 60 includes a plurality of servomotors M1, encoders E1, and speed reducers (not shown) so as to correspond to a plurality of joints 64 of the arm portion 61. The encoders E1 detect the rotation angles of the servomotors M1. The speed reducers slow down rotation of the servomotors M1 to increase the torques.

As shown in FIG. 10, the translation mechanism 70 includes the servomotor M2 to rotate the rotating body provided in the driven unit 4a of the surgical instrument 4, a servomotor M3 to translate the surgical instrument 4, encoders E2 and E3, and speed reducers (not shown). The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels (not shown) of the medical cart 3, respectively, encoders E5, and speed reducers (not shown). The encoders E5 detect the rotation angles of the servomotors M5. The speed reducers slow down rotation of the servomotors M5 to increase the torques.

The controller 31 of the medical cart 3 includes an arm controller 31a to control movement of the plurality of manipulator arms 60 based on commands, and a positioner controller 31b to control movement of the positioner 40 and driving of the front wheels (not shown) of the medical cart 3 based on commands. Servo controllers C1 that control the servomotors M1 to drive the manipulator arm 60 are electrically connected to the arm controller 31a. The encoders E1 to detect the rotation angles of the servomotors M1 are electrically connected to the servo controllers C1.

A servo controller C2 that controls the servomotor M2 to drive the surgical instrument 4 is electrically connected to the arm controller 31a. The encoder E2 to detect the rotation angle of the servomotor M2 is electrically connected to the servo controller C2. A servo controller C3 that controls the servomotor M3 to translate the translation mechanism 70 is electrically connected to the arm controller 31a. The encoder E3 to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands (input position signal $x_{in}$) input from the arm controller 31a and the rotation angles detected by the encoders E1 (E2 or E3), and output the torque commands to the servomotors M1 (M2 or M3). Thus, the manipulator arm 60 is moved according to the operation command input to the remote operation device 2.

Figure 11:
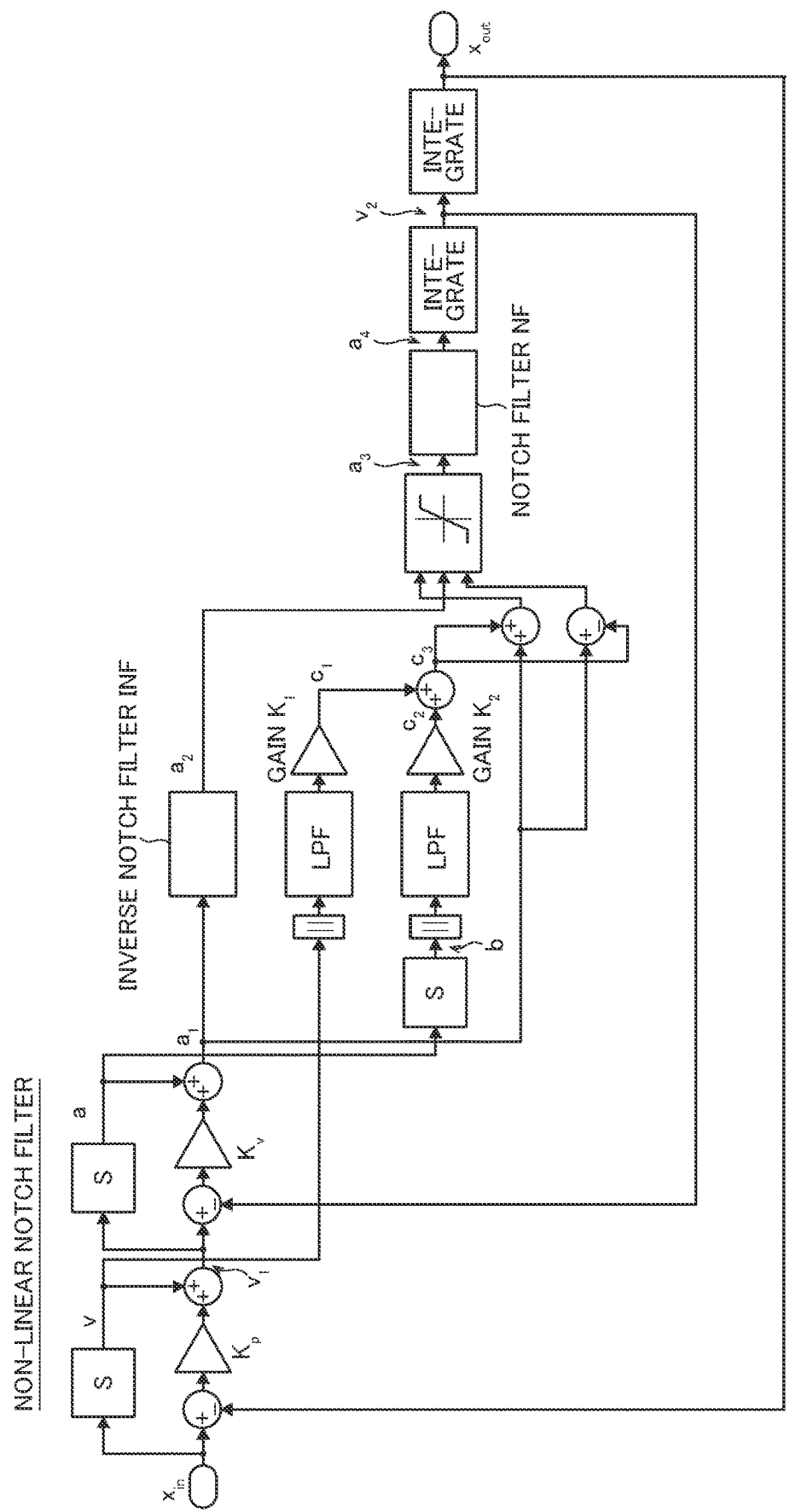
FIG. 11 is a block diagram of a servo controller (non-linear notch filter) according to the embodiment of the present disclosure.
Figure 12:
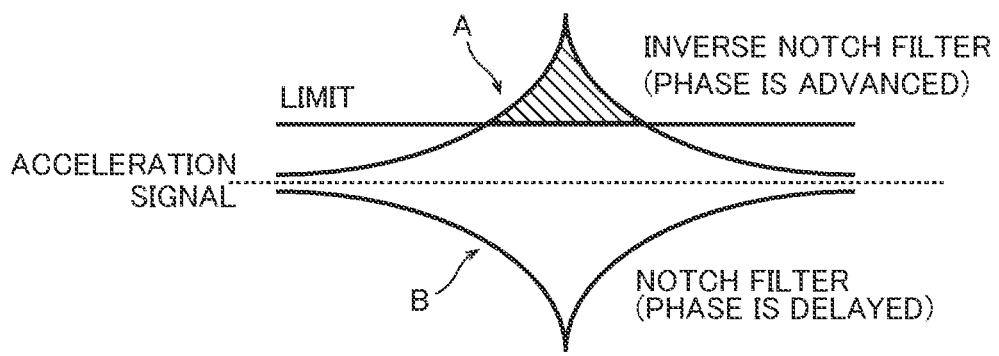
FIG. 12 is an image diagram for illustrating the non-linear notch filter according to the embodiment of the present disclosure.

Specifically, in this embodiment, as shown in FIG. 11, the servo controllers C1 calculate an operation speed signal (acceleration signal a in this embodiment) of any one of a speed signal v, an acceleration signal a, and a jerk signal b based on the input position signal $x_{in}$ indicating the position of the surgical instrument 4. Specifically, the servo controllers C1 calculate the speed signal v by differentiating (subtracting) the input position signal $x_{in}$. Furthermore, the servo controllers C1 subtract an output position signal $x_{out}$ fed back from the input position signal $x_{in}$, and multiply the subtracted value by a position gain $K_p$. Then, the servo controllers C1 calculate a speed signal $v_1$ by adding the value obtained by multiplying the subtracted value by the position gain $K_p$ to the speed signal v. The servo controllers C1 are examples of a "controller" or a "control device of a robotic surgical system" in the claims. The acceleration signal a is an example of an "operation speed signal" in the claims.

The servo controllers C1 calculate the acceleration signal a by differentiating (subtracting) the speed signal $v_1$. Furthermore, the servo controllers C1 subtract a filtered speed signal $v_2$ fed back from the speed signal $v_1$ and multiply the subtracted value by a speed gain $K_v$. Then, the servo controllers C1 calculate an acceleration signal $a_1$ by adding the value obtained by multiplying the subtracted value by the speed gain $K_v$ to the acceleration signal a.

Then, the servo controllers C1 apply an inverse notch filter INF that amplifies a component of a first frequency band $H_1$ (see FIG. 16) of the calculated acceleration signal $a_1$ to calculate an inverse filtered acceleration signal $a_2$. The first frequency band $H_1$ is a frequency band corresponding to hands movement of a user who operates the operation manipulator arms 21, for example. As shown in an image diagram of FIG. 12, the inverse notch filter INF is applied such that the component of the first frequency band $H_1$ of the acceleration signal $a_1$ is amplified (see arrow A in FIG. 12). The inverse notch filter INF is applied such that the phase (control) of the inverse filtered acceleration signal $a_2$ is advanced. The inverse notch filter INF is an example of a "first filter" in the claims. The inverse filtered acceleration signal $a_2$ is an example of a "first filtered signal" or a "first filtered acceleration signal" in the claims.

As shown in FIG. 11, the servo controllers C1 limit the inverse filtered acceleration signal $a_2$ and calculate a limited acceleration signal $a_3$. As shown in the image diagram of FIG. 12, a portion of the amplified inverse filtered acceleration signal $a_2$ that exceeds a limit value is removed (see a hatched region of FIG. 12). Although the limit value is shown to be constant in FIG. 12, the limit value changes according to the amplitude of the acceleration signal a, as described below. The limited acceleration signal $a_3$ is an example of a "limited signal" in the claims.

As shown in FIG. 11, the servo controllers C1 apply a notch filter NF that reduces the component of the first frequency band $H_1$ to the limited acceleration signal $a_3$ to calculate a filtered acceleration signal $a_4$. As shown in the image diagram of FIG. 12, the notch filter NF is applied such that the component of the first frequency band $H_1$ of the limited acceleration signal $a_3$ is reduced (see arrow B in FIG. 12). The notch filter NF is applied such that the phase (control) of the filtered acceleration signal $a_4$ is delayed. The notch filter NF is an example of a "second filter" in the claims. The filtered acceleration signal $a_4$ is an example of a "second filtered signal" or a "second filtered acceleration signal" in the claims.

Specifically, instead of reducing the component of the first frequency band $H_1$ of the limited acceleration signal $a_3$ by one notch filter NF, a plurality of non-linear notch filters (notch filters including the inverse notch filter INF and the notch filter NF) are arranged in series, and the plurality of non-linear notch filters reduce different frequency band components within the range of the first frequency band $H_1$.

Figure 13:
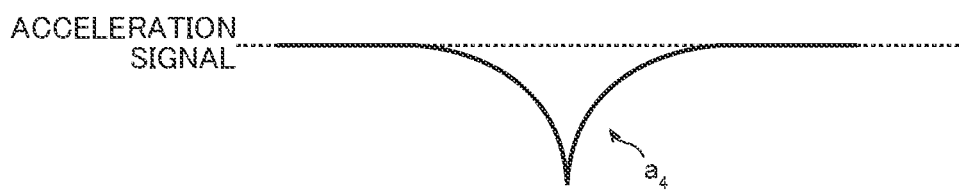
FIG. 13 is another image diagram for illustrating the non-linear notch filter according to the embodiment of the present disclosure.
Figure 14:
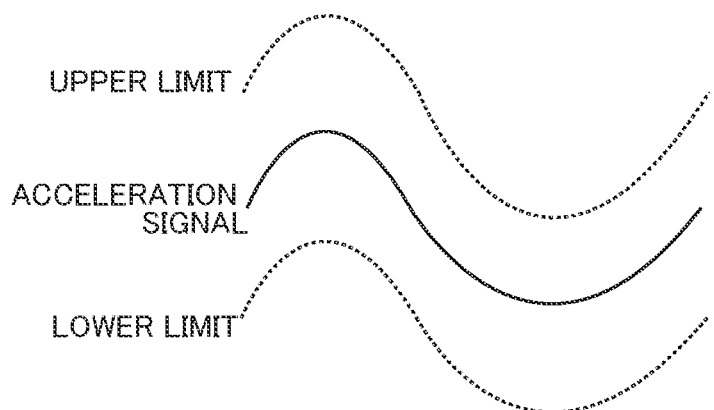
FIG. 14 is an image diagram showing a range of acceleration limits according to the embodiment of the present disclosure.

Then, both the inverse notch filter INF and the notch filter NF are applied such that the advance of control (phase) by the inverse notch filter INF and a control delay (phase) by the notch filter NF are canceled out. Then, as shown in FIG. 13, the filtered acceleration signal $a_4$ in which the component of the first frequency band $H_1$ is reduced and the phase delay is reduced is obtained.

As shown in FIG. 11, in this embodiment, the servo controllers C1 calculate the filtered speed signal $v_2$ and the output position signal $x_{out}$ based on the filtered acceleration signal $a_4$ to which the notch filter NF has been applied. Specifically, the servo controllers C1 calculate the filtered speed signal $v_2$ by integrating the filtered acceleration signal $a_4$. Furthermore, the servo controllers C1 calculate the output position signal $x_{out}$ by integrating the filtered speed signal $v_2$. Then, the servo controllers C1 feed back the filtered speed signal $v_2$ and the output position signal $x_{out}$. Specifically, the servo controllers C1 subtract the filtered speed signal $v_2$ one sample before (one cycle before in a control cycle) from the speed signal $v_1$. Furthermore, the servo controllers C1 subtract the output position signal $x_{out}$ one sample before from the input position signal $x_{in}$.

As described above, the notch filters including the inverse notch filter INF and the notch filter NF are non-linear notch filters. The "non-linear notch filters" refer to notch filters in which a differential equation becomes non-linear when the notch filters are represented by the differential equation.

In this embodiment, as shown in FIG. 11, the servo controllers C1 calculate an upper limit and a lower limit of the limit for the inverse filtered acceleration signal $a_2$ based on the speed signal $v_1$ and the jerk signal b. Specifically, the servo controllers C1 calculate an absolute value of the speed signal v and applies a low-pass filter (LPF) to the absolute value of the speed signal v. Then, the servo controllers C1 calculate a value $c_1$ by multiplying the value to which the LPF has been applied by a gain $K_1$.

The servo controllers C1 differentiate (subtract) the acceleration signal a to calculate the jerk signal b. Furthermore, the servo controllers C1 calculate an absolute value of the jerk signal b and applies the LPF to the absolute value of the jerk signal b. Then, the servo controllers C1 calculate a value $c_2$ by multiplying the value to which the LPF has been applied by a gain $K_2$.

Then, the servo controllers C1 add the value ci and the value $c_2$ to calculate a value $c_3$, and add the value $c_3$ and the acceleration signal $a_1$ to calculate the upper limit for the inverse filtered acceleration signal $a_2$. Furthermore, the servo controllers C1 subtract the value $c_3$ from the acceleration signal $a_1$ to calculate the lower limit for the inverse filtered acceleration signal $a_2$. Thus, the width of the limit (a width between the upper limit and the lower limit) for the inverse filtered acceleration signal $a_2$ is calculated.

In this embodiment, the servo controllers C1 calculate the upper limit and the lower limit of the limit according to the amplitude of the acceleration signal a. As shown in an image diagram of the limit value in FIG. 14, the acceleration signal a (inverse filtered acceleration signal $a_2$) changes into a waveform. Then, the upper limit and the lower limit of the limit change according to the waveform of the inverse filtered acceleration signal $a_2$.

Figure 15:
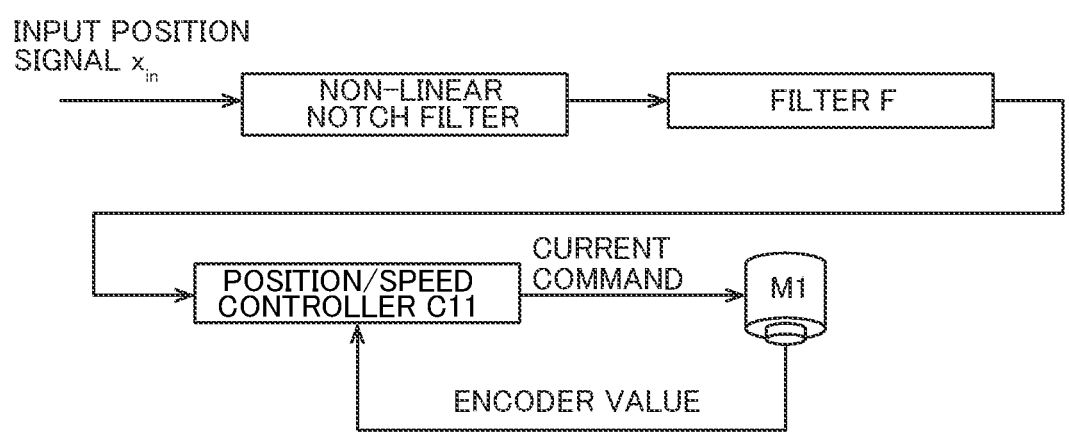
FIG. 15 is a block diagram of a servo controller (a non-linear notch filter and a linear filter) according to the embodiment of the present disclosure.

In this embodiment, as shown in FIG. 15, the servo controllers C1 apply a filter F that reduces a component of a second frequency band $H_2$ (see FIG. 16) that is smaller than the first frequency band $H_1$ of the acceleration signal a to the component of the second frequency band $H_2$. Specifically, the second frequency band $H_2$ is a frequency band corresponding to the natural frequency of the medical manipulator 1, for example. More specifically, the servo controllers C1 apply the filter F to the output position signal $x_{out}$ (after the non-linear notch filters are applied). The filter F is a linear filter. That is, when the filter F is represented by a differential equation, the differential equation becomes linear. The filter F is an example of a "third filter" in the claims.

The servo controllers C1 transmit the output position signal $x_{out}$ to which the filter F has been applied to a position/speed controller C11. The position/speed controller C11 transmits current commands to the servomotors M1. Furthermore, the position/speed controller C11 generates the current commands based on the rotation positions (encoder values) of the servomotors M1 detected by the encoders E1.

Improvement of the control delay by the non-linear notch filters (application of the inverse notch filter INF and the notch filter NF) according to this embodiment is now described with reference to FIGS. 16 to 18.

Figure 16:
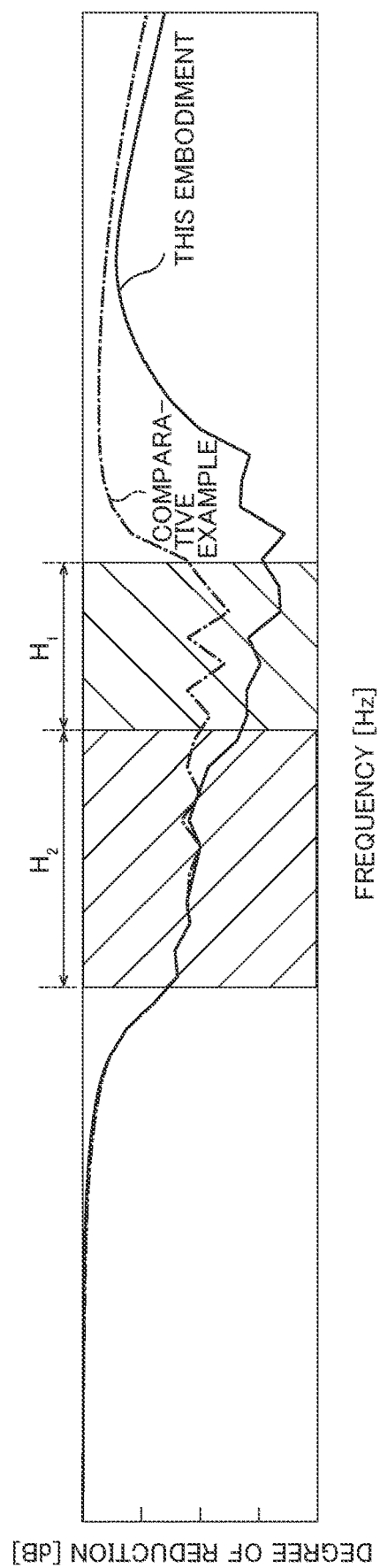
FIG. 16 is a diagram showing a relationship between a frequency and the magnitude of acceleration.

In FIG. 16, the horizontal axis represents a frequency, and the vertical axis represents the degree of reduction of the frequency component of the acceleration signal a calculated based on the input position signal $x_{in}$. In FIGS. 17 and 18, the horizontal axis represents a frequency, and the vertical axis represents a control delay (phase). One-dot chain lines in FIGS. 16 to 18 represent a case in which only the notch filter has been applied to the acceleration signal a (acceleration signal a before filter application) (comparative example). In the comparative example, it has been confirmed that the component of the frequency band of the acceleration signal a corresponding to the hands movement is reduced, and vibrations due to the hands movement are reduced. On the other hand, as shown in FIGS. 17 and 18, in the comparative example (see the one-dot chain lines), it has been confirmed that the control delay (phase) is increased with respect to the acceleration signal a (not shown) before filter application.

Figure 17:
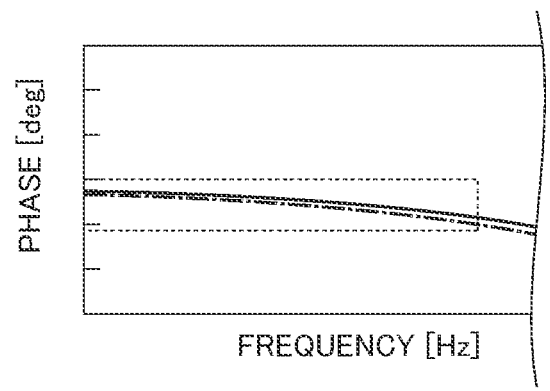
FIG. 17 is a diagram showing a relationship between a frequency and a control delay (phase).
Figure 18:
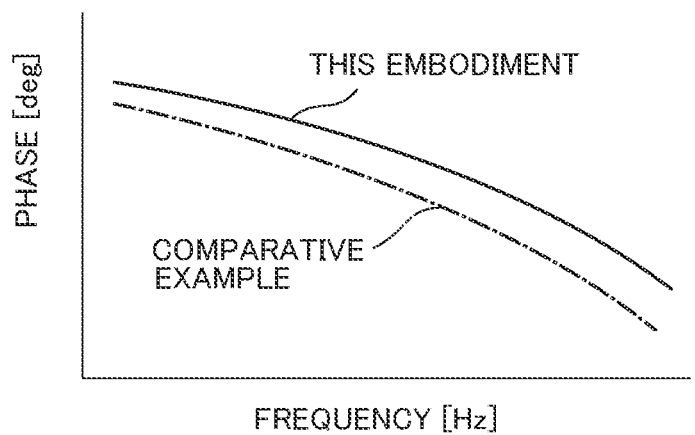
FIG. 18 is an enlarged view of FIG. 17.

Solid lines in FIGS. 16 to 18 represent a case in which the non-linear notch filters according to this embodiment have been applied to the acceleration signal a (acceleration signal a before filter application). It has been confirmed that the component of the frequency band of the acceleration signal a corresponding to the hands movement is reduced (vibrations are reduced), and vibrations due to the hands movement are reduced when the non-linear notch filters have been applied to the acceleration signal a. Furthermore, as shown in FIGS. 17 and 18, it has been confirmed that the control delay (phase) is reduced with respect to that before non-linear notch filters application (not shown) when the non-linear notch filters have been applied (see the solid lines). That is, it has been confirmed that the non-linear notch filters according to this embodiment can reduce the control delay while significantly reducing or preventing vibrations of the medical manipulator 1 caused by the hands movement of the user.

As shown in FIG. 10, the controller 31 (arm controller 31a) operates the manipulator arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the manipulator arm 60 is moved according to the operation command input to the joystick 82.

The controller 31 (arm controller 31a) operates the manipulator arm 60 based on an input signal from the switch unit 83 of the operation unit 80. Specifically, the arm controller 31a generates a position command based on the input signal (operation command) input from the switch unit 83 and the rotation angle detected by the encoders E1 or the encoder E3, and outputs the position command to the servo controllers C1 or the servo controller C3. The servo controllers C1 or the servo controller C3 generates a torque command based on the position command input from the arm controller 31a and the rotation angle detected by the encoders E1 or the encoder E3, and outputs the torque command to the servomotors M1 or the servomotor M3. Thus, the manipulator arm 60 is moved according to the operation command input to the switch unit 83.

As shown in FIG. 10, servo controllers C4 that control the servomotors M4 to move the positioner 40 are electrically connected to the positioner controller 31b. The encoders E4 to detect the rotation angles of the servomotors M4 are electrically connected to the servo controllers C4. Servo controllers C5 that control the servomotors M5 to drive the front wheels (not shown) of the medical cart 3 are electrically connected to the positioner controller 31b. The encoders E5 to detect the rotation angles of the servomotors M5 are electrically connected to the servo controllers C5.

An operation command related to setting of a preparation position, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 according to an operation command from the input 33.

Control Method of Surgical System

A control method of the surgical system 100 is now described with reference to FIG. 19.

First, in step S1, the servo controllers C1 receive an operation on the surgical instrument 4.

Then, in step S2, the servo controllers C1 calculate the operation speed signal (the acceleration signal a in this embodiment) of any one of the speed signal, the acceleration signal, and the jerk signal based on the input position signal $x_{in}$ of the surgical instrument 4 corresponding to the received operation.

Then, in step S3, the servo controllers C1 apply the inverse notch filter INF that amplifies the component of the frequency band of the calculated acceleration signal a to calculate the inverse filtered acceleration signal $a_2$.

Then, in step S4, the servo controllers C1 limit the inverse filtered acceleration signal $a_2$ to calculate the limited acceleration signal $a_3$. The servo controllers C1 calculate the speed signal v and the jerk signal b, and calculate the upper limit and the lower limit of the limit for the inverse filtered acceleration signal $a_2$ based on the speed signal v and the jerk signal b.

Then, in step S5, the servo controllers C1 apply the notch filter NF that reduces the component of the first frequency band $H_1$ to the limited acceleration signal $a_3$ to calculate the filtered acceleration signal $a_4$.

Then, in step S6, the servo controllers C1 calculate the output position signal $x_{out}$ indicating the position of the surgical instrument 4 based on the filtered acceleration signal $a_4$. Specifically, the servo controllers C1 integrate the filtered acceleration signal $a_4$ to calculate the filtered speed signal $v_2$, and integrate the filtered speed signal $v_2$ to calculate the output position signal $x_{out}$.

Then, in step S7, the servo controllers C1 feed back the filtered speed signal $v_2$ and the output position signal $x_{out}$.

The operations in step S1 to step S7 described above are constantly performed during the operation of the manipulator arm 60, and are performed for each of the plurality of manipulator arms 60.

Advantages of this Embodiment

According to this embodiment, the following advantages are achieved.

Advantages of Medical Manipulator

According to this embodiment, as described above, the servo controllers C1 are configured or programmed to calculate the acceleration signal a, apply the inverse notch filter INF that amplifies the component of the first frequency band $H_1$ of the calculated acceleration signal a to calculate the inverse filtered acceleration signal $a_2$, limit the inverse filtered acceleration signal $a_2$ to calculate the limited acceleration signal $a_3$, apply the notch filter NF that reduces the component of the first frequency band $H_1$ to the limited acceleration signal $a_3$ to calculate the filtered acceleration signal $a_4$, and calculate the output position signal $x_{out}$ of the surgical instrument 4 based on the filtered acceleration signal $a_4$. When only the notch filter NF is applied without applying the inverse notch filter INF, the component of the first frequency band $H_1$ of the acceleration signal a is reduced, and thus the output position signal $x_{out}$ of the surgical instrument 4 is calculated based on the acceleration signal a after component reduction such that vibrations of the acceleration signal a can be reduced. On the other hand, the control delay (phase delay) occurs due to application of the notch filter NF. Therefore, both the inverse notch filter INF and the notch filter NF are applied as described above such that the advance of the control (phase) by the inverse notch filter INF and the delay of the control (phase) by the notch filter NF are canceled out, and thus the control delay can be reduced. When the inverse notch filter INF and the notch filter NF are simply applied, nothing acts on the acceleration signal a. Therefore, as described above, the inverse filtered acceleration signal $a_2$ is limited, and the limited acceleration signal $a_3$ is calculated such that a relatively large component of the first frequency band $H_1$ of the acceleration signal a is removed. Thus, the output position signal $x_{out}$ of the surgical instrument 4 is calculated based on the limited acceleration signal $a_3$ after removal such that vibrations of the acceleration signal a (signal) can be reduced. Consequently, the control delay can be reduced while vibrations in the signal (acceleration signal a) transmitted from the remote operation device 2 side to the medical manipulator 1 side are reduced to reduce vibrations of the medical manipulator 1.

According to this embodiment, as described above, the servo controllers C1 are configured or programmed to apply the filter F that reduces the component of the second frequency band $H_2$ that is smaller than the first frequency band $H_1$ to the component of the second frequency band $H_2$. Accordingly, the control delay is reduced by applying both the inverse notch filter INF and the notch filter NF to the component of the first frequency band $H_1$, and thus even when the degree of reduction of the component of the second frequency band $H_2$ by the filter F is increased by the amount of this reduction in control delay (that is, even when the control delay by the filter F is increased), an increase in the control delay of the entire surgical system 100 can be significantly reduced or prevented.

According to this embodiment, as described above, the first frequency band $H_1$ is a frequency band corresponding to the hands movement of the user who operates the operation manipulator arms 21, and the second frequency band $H_2$ is a frequency band corresponding to the natural frequency of the medical manipulator 1. Accordingly, vibrations of the signal (acceleration signal a) caused by the hands movement of the user who operates the operation manipulator arms 21 are reduced, and thus vibrations of the medical manipulator 1 caused by the hands movement of the user can be significantly reduced or prevented. Furthermore, vibrations of the natural frequency of the medical manipulator 1 are reduced, and thus natural vibrations of the medical manipulator 1 can be reduced.

According to this embodiment, as described above, the servo controllers C1 are configured or programmed to calculate the acceleration signal a by differentiating the input position signal $x_{in}$ of the surgical instrument 4. Accordingly, the acceleration signal a is reduced, and thus vibrations of the medical manipulator 1 caused by the hands movement of the user can be significantly reduced or prevented.

According to this embodiment, as described above, the servo controllers C1 are configured or programmed to calculate the speed signal v and the jerk signal b based on the input position signal $x_{in}$, apply the inverse notch filter INF to the calculated acceleration signal a to calculate the inverse filtered acceleration signal $a_2$, and calculate the upper limit and the lower limit of the limit for the inverse filtered acceleration signal $a_2$ based on the calculated speed signal v and jerk signal b. Accordingly, the upper limit and the lower limit of the limit can be adjusted to make the frequency band to which the inverse notch filter INF is to be applied stand out (in other words, to significantly reduce or prevent application of the inverse notch filter INF to the frequency band to which the inverse notch filter INF is not to be applied) based on both the speed signal v and the jerk signal b.

According to this embodiment, as described above, the servo controllers C1 are configured or programmed to calculate the upper limit and the lower limit of the limit according to the amplitude of the acceleration signal a. Accordingly, unlike a case in which the limit for the inverse filtered acceleration signal $a_2$ is a constant value, the inverse filtered acceleration signal $a_2$ having an amplitude (wave shape) can be appropriately limited.

According to this embodiment, as described above, the servo controllers C1 are configured or programmed to calculate the filtered speed signal $v_2$ and the output position signal $x_{out}$ based on the filtered acceleration signal $a_4$ to which the notch filter NF has been applied, and feed back the filtered speed signal $v_2$ and the output position signal $x_{out}$. Accordingly, even when a position corresponding to the input position signal $x_{in}$ of the surgical instrument 4 and the position of the manipulator arm 60 deviate from each other due to limiting the inverse filtered acceleration signal $a_2$, the position deviation can be reduced by feedback control.

Advantages of Control Method of Surgical System

According to this embodiment, as described above, the control method of the surgical system 100 includes applying the inverse notch filter INF to the calculated acceleration signal a, limiting the inverse filtered acceleration signal $a_2$, and applying the notch filter NF to the limited acceleration signal $a_3$. Accordingly, the control delay can be reduced while vibrations in the signal (acceleration signal a) transmitted from the remote operation device 2 side to the medical manipulator 1 side are reduced to reduce vibrations of the medical manipulator 1.

MODIFIED EXAMPLES

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the non-linear notch filters are applied by the servo controllers C1 in the aforementioned embodiment, the present disclosure is not limited to this. For example, the non-linear notch filters may alternatively be applied in the controller 31 of the medical manipulator 1 or the remote operation device 2.

While the non-linear notch filters are applied to the acceleration signal a in the aforementioned embodiment, the present disclosure is not limited to this. For example, the non-linear notch filters may alternatively be applied to the speed signal v or the jerk signal b.

While the upper limit and the lower limit of the limit are calculated based on the speed signal v and the jerk signal b in the aforementioned embodiment, the present disclosure is not limited to this. In the present disclosure, the upper limit and the lower limit of the limit may alternatively be calculated based on an index other than the speed signal v and the jerk signal b.

While the four manipulator arms 60 are provided in the aforementioned embodiment, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in the aforementioned embodiment, the present disclosure is not limited to this. For example, each of the arm portion 61 and the positioner 40 may alternatively include an articulated robot having an axis configuration (six axes or eight axes, for example) other than the 7-axis articulated robot.

While the medical manipulator 1 includes the medical cart 3, the positioner 40, the arm base 50, and the manipulator arms 60 in the aforementioned embodiment, the present disclosure is not limited to this. For example, the medical manipulator 1 may not include the medical cart 3, the positioner 40, or the arm base 50, but may include only the manipulator arms 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
   a patient-side apparatus including a manipulator arm to which a surgical instrument is attached to a tip end side of the manipulator arm;
   an operator-side apparatus including a manipulator to receive an operation for operating the surgical instrument; and
   a controller configured or programmed to output an output position signal indicating a position of the surgical instrument based on an input position signal indicating the position of the surgical instrument corresponding to the received operation, the controller being configured or programmed to control operation of the surgical instrument; wherein
   the controller is configured or programmed to:
      calculate an operation speed signal that is a signal relating to an operation speed of the surgical instrument based on the input position signal of the operator-side apparatus;
      apply an inverse notch filter that amplifies a component of a first frequency band corresponding to vibrational movements of the manipulator of the calculated operation speed signal to the operation speed signal to calculate a first filtered signal;
      limit the first filtered signal to calculate a limited signal;
      apply a notch filter that reduces the component of the first frequency band to the limited signal to calculate a second filtered signal; and
      calculate the output position signal based on the second filtered signal.

2. The robotic surgical system according to claim 1, wherein the controller is configured or programmed to apply a linear filter that reduces a component of a second frequency band that is smaller than the first frequency band to the component of the second frequency band.

3. The robotic surgical system according to claim 2, wherein
   the second frequency band is a frequency band corresponding to a natural frequency of the patient-side apparatus.

4. The robotic surgical system according to claim 1, wherein the controller is configured or programmed to calculate an acceleration signal as the operation speed signal by differentiating the input position signal.

5. The robotic surgical system according to claim 4, wherein
   the controller is configured or programmed to:
      calculate a speed signal and a jerk signal as the operation speed signal based on the input position signal;
      apply the inverse notch filter to the calculated acceleration signal to calculate a first filtered acceleration signal; and
      calculate an upper limit and a lower limit of a limit for the first filtered acceleration signal based on the calculated speed signal and jerk signal.

6. The robotic surgical system according to claim 5, wherein the controller is configured or programmed to calculate the upper limit and the lower limit of the limit according to a change in an amplitude of the acceleration signal.

7. The robotic surgical system according to claim 4, wherein
   the controller is configured or programmed to:
      calculate a second filtered speed signal and the output position signal based on a second filtered acceleration signal to which the second filter has been applied; and
      feed back the second filtered speed signal and the output position signal.

8. A control device of a robotic surgical system, the robotic surgical system including a patient-side apparatus including a manipulator arm to which a surgical instrument is attached to a tip end side of the manipulator arm, and an operator-side apparatus including a manipulator to receive an operation for operating the surgical instrument, the control device comprising:
   a controller configured or programmed to output an output position signal indicating a position of the surgical instrument based on an input position signal indicating the position of the surgical instrument corresponding to the received operation, the controller being configured or programmed to control operation of the surgical instrument; wherein
   the controller is configured or programmed to:
      calculate an operation speed signal that is a signal relating to an operation speed of the surgical instrument based on the input position signal of the operator-side apparatus;

apply an inverse notch filter that amplifies a component of a first frequency band corresponding to vibrational movements of the manipulator of the calculated operation speed signal to the operation speed signal to calculate a first filtered signal;

limit the first filtered signal to calculate a limited signal;

apply a notch filter that reduces the component of the first frequency band to the limited signal to calculate a second filtered signal; and calculate the output position signal based on the second filtered signal.

9. The control device of the robotic surgical system according to claim 8, wherein the controller is configured or programmed to apply a linear filter that reduces a component of a second frequency band that is smaller than the first frequency band to the component of the second frequency band.

10. The control device of the robotic surgical system according to claim 9, wherein
the second frequency band is a frequency band corresponding to a natural frequency of the patient-side apparatus.

11. The control device of the robotic surgical system according to claim 8, wherein the controller is configured or programmed to calculate an acceleration signal as the operation speed signal by differentiating the input position signal.

12. The control device of the robotic surgical system according to claim 11, wherein
the controller is configured or programmed to:
calculate a speed signal and a jerk signal as the operation speed signal based on the input position signal;
apply the inverse notch filter to the calculated acceleration signal to calculate a first filtered acceleration signal; and
calculate an upper limit and a lower limit of a limit for the first filtered acceleration signal based on the calculated speed signal and jerk signal.

13. The control device of the robotic surgical system according to claim 12, wherein the controller is configured or programmed to calculate the upper limit and the lower limit of the limit according to a change in an amplitude of the acceleration signal.

14. A control method of a robotic surgical system, the robotic surgical system including a patient-side apparatus including a manipulator arm to which a surgical instrument is attached to a tip end side of the manipulator arm, an operator-side apparatus including a manipulator to receive an operation for operating the surgical instrument, and a controller, the control method comprising:
receiving an operation on the surgical instrument;
calculating an operation speed signal that is a signal relating to an operation speed of the surgical instrument based on an input position signal indicating a position of the surgical instrument corresponding to the received operation;

applying an inverse notch filter that amplifies a component of a first frequency band of the calculated operation speed signal to the operation speed signal to calculate a first filtered signal;

limiting the first filtered signal to calculate a limited signal;

applying a second filter that reduces the component of the first frequency band to the limited signal to calculate a second filtered signal; and calculating an output position signal indicating the position of the surgical instrument based on the second filtered signal.

15. The control method of the robotic surgical system according to claim 14, wherein the controller is configured or programmed to apply a linear filter that reduces a component of a second frequency band that is smaller than the first frequency band to the component of the second frequency band.

16. The control method of the robotic surgical system according to claim 15, wherein
the first frequency band is a frequency band corresponding to movements of the manipulator; and
the second frequency band is a frequency band corresponding to a natural frequency of the patient-side apparatus.

17. The control method of the robotic surgical system according to claim 14, wherein the controller is configured or programmed to calculate an acceleration signal as the operation speed signal by differentiating the input position signal.

18. The control method of the robotic surgical system according to claim 17, wherein
the controller is configured or programmed to:
calculate a speed signal and a jerk signal as the operation speed signal based on the input position signal;
apply the inverse notch filter to the calculated acceleration signal to calculate a first filtered acceleration signal; and
calculate an upper limit and a lower limit of a limit for the first filtered acceleration signal based on the calculated speed signal and jerk signal.

19. The control method of the robotic surgical system according to claim 18, wherein the controller is configured or programmed to calculate the upper limit and the lower limit of the limit according to a change in an amplitude of the acceleration signal.

20. The control method of the robotic surgical system according to claim 17, wherein
the controller is configured or programmed to:
calculate a second filtered speed signal and the output position signal based on a second filtered acceleration signal to which the second filter has been applied; and
feed back the second filtered speed signal and the output position signal.

* * * * *